US006887465B1

(12) United States Patent
Reniero et al.

(10) Patent No.: US 6,887,465 B1
(45) Date of Patent: May 3, 2005

(54) LACTOBACILLUS STRAINS CAPABLE OF PREVENTING DIARRHOEA CAUSED BY PATHOGENIC BACTERIA AND ROTAVIRUSES

(75) Inventors: Roberto Reniero, Le Mont-Pelerin (CH); Harald Bruessow, La Tour de Peilz (CH); Florence Rochat, Montreux (CH); Thierry Von Der Weid, Paudex (CH); Stephanie Blum-Speriesen, Lausanne (CH); Jean-Richard Neeser, Savigny (CH); Alain Servin, Chateney-Malabry (FR)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 09/936,542

(22) PCT Filed: Mar. 2, 2000

(86) PCT No.: PCT/EP00/01798

§ 371 (c)(1),
(2), (4) Date: Jan. 18, 2002

(87) PCT Pub. No.: WO00/53202

PCT Pub. Date: Sep. 14, 2000

(30) Foreign Application Priority Data

Mar. 11, 1999 (EP) .......................................... 99104922
Mar. 11, 1999 (EP) .......................................... 99104924

(51) Int. Cl.$^7$ .......................... A23C 9/12; A23K 1/18; A23L 1/28; A01N 63/00; C12N 1/20
(52) U.S. Cl. .................. 424/93.45; 426/61; 426/531; 426/807; 435/252.9; 435/853
(58) Field of Search .................... 424/93.45, 93.1; 426/61, 531, 807, 7, 34; 435/252.9, 853, 252.1, 822

(56) References Cited

U.S. PATENT DOCUMENTS 5,837,238 A    11/1998    Casas et al.

FOREIGN PATENT DOCUMENTS

| EP | 0 577 903 | 1/1994 |
|----|-----------|--------|
| EP | 0 861 905 | 9/1998 |
| WO | 95/33046  | 12/1995 |
| WO | 98/06411  | 2/1998 |

OTHER PUBLICATIONS

Prasad, J. et al., "Selection and characterization of Lactobacillus and Bifidobacterium strains for use as probiotics," International Dairy Journal, vol. 8, No. 12, 1998, pp 993–1102.

Miettinen, M. et al., "Lactobacilli and Streptococci Induce Interleukin–12 (IL–12), IL–18, and Gamma Interferon Production in Human Peripheral Blood Mononuclear Cells," Infection and Immunity, Dec. 1998, pp 6058–6062.

Tuomola, E. et al., "Adhesion of some probiotic and dairy Lactobacillus strains to Caco–2 cell cultures," International Journal of Food Microbiology, vol. 41, 1998, pp 45–51.

Kaila, M. et al., "Viable versus inactivated lactobacillus strain GG in acute rotavirus diarrhoea," archives of Disease in Childhood, vol. 72, No. 1, 1995, pp 51–53.

Majamaa, H. et al., "Lactic Acid Bacteria in the Treatment of Acute Rotavirus Gastoenteritis," Journal of Pediatric Gastroenterology and Nutrition, vol. 20, 1995, pp 333–338.

*Primary Examiner*—Jon Weber
*Assistant Examiner*—Deborah K. Ware
(74) *Attorney, Agent, or Firm*—Bell, Boyd & Lloyd LLC (57) ABSTRACT

Novel microorganisms of the family Lactobacillaceae and pharmaceutical compositions, food and methods of using same are provided. The microorganisms have the ability of preventing colonization of the intestine with pathogenic bacteria causing diarrhea and of preventing infection of intestinal epithelial cells by *rotaviruses*. The microorganisms can be used for the preparation of an ingestable support and to compositions containing same.

8 Claims, 9 Drawing Sheets

Fig. 4 Induction of cytokine mRNA by LAB in mouse macrophages

LACTOBACILLUS STRAINS CAPABLE OF PREVENTING DIARRHOEA CAUSED BY PATHOGENIC BACTERIA AND ROTAVIRUSES

The present invention pertains to novel microorganisms of the genus *Lactobacillus*, that are useful in preventing diarrhoea brought about by both pathogenic bacteria and *rotaviruses*, respectively. In particular, the present invention relates to the use of said microorganisms for the preparation of an ingestable support and to a composition containing the same.

Organisms that produce lactic acid as a major metabolic component have been known for a long time. These bacteria may be found in milk or in milk processing factories. respectively, living or decaying plants but also in the intestine of man and animals. These microorganisms, summarized under the term "lactic acid bacteria", represent a rather inhomogeneous group and comprise e.g. the genera *Lactococcus, Lactobacillus, Streptococcus, Bifidobacterium, Pediococcus* etc.

Lactic acid bacteria have been utilized as fermenting agents for the preservation of food taking benefit of a low pH and the action of fermentation products generated during the fermentative activity thereof to inhibit the growth of spoilage bacteria. To this end, lactic acid bacteria have been used for preparing a variety of different foodstuff such as cheese, yogurt and other fermented diary products from milk.

Quite recently lactic acid bacteria have attracted a great deal of attention in that some strains have been found to exhibit valuable properties to man and animals upon ingestion In particular, specific strains of the genus *Lactobacillus* or *Bifidobacterium* have been found to be able to colonize the intestinal mucosa and to assist in the maintenance of the well-being of man and animal.

In this respect, EP 0 768 375 discloses specific strains of the genus *Bifidobacterium*, that are capable to become implanted in the intestinal flora and may adhere to intestinal cells.

These Bifidobacteria are reported to assist in immunomodulation and being capable to competitively exclude adhesion of pathogenic bacteria to intestinal cells, thus assisting in the maintenance of the individual's health.

During the last few years research has also focused on the potential use of lactic acid bacteria as probiotic agents. Probiotics are considered to be viable microbial preparations which promote the individual's health by preserving the natural microflora in the intestine. A microbial preparation may be commonly accepted as a probiotic in case the effectual microbes thereof and their mode of action are known. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach.

In this respect, WO 97/00078 discloses a specific strain, termed *Lactobacillus* GG (ATCC 53103). as such a probiotic. The microorganism is particularly employed in a method of preventing or treating food induced hypersensitivity reactions in that it is administered to a recipient together with a food material that has been subjected to a hydrolysis treatment with pepsin and/or trypsin. The *Lactobacillus* strain selected is described as exhibiting adhesive and colonizing properties and showing a protease enzyme system, so that the protein material contained in the foodstuff to be administered is further hydrolyzed by means of proteases secreted by the specific *Lactobacillus* strain. The method discussed in this document shall eventually result in the uptake of protein material by the gut that does not show a substantial amount of allergenic material anymore.

Further, in EP 0 577 903 reference is made to the use of such lactic acid bacteria having the ability of replacing *Heliobacter pylori*, the acknowledged cause for the development of ulcer, in the preparation of a support intended for the therapeutic or prophylactic treatment of an ulcer associated with the action of *Heliobacter pylori*.

In the intervening document WO 99/29833 a particular strain, LMG P 17806, is described that harbors three plasmids of a defined size. This strain is described to be able to prevent intestinal cells from being invaded by *salmonella typhimurium*.

In knowledge of the valuable properties particular strains of lactic acid bacteria may provide, there is a desire in the art for additional lactic acid bacterial strains that are beneficial to the well being of man and/or animal.

SUMMARY OF THE INVENTION

Consequently, a problem of the present invention is to provide additional bacterial strains that exhibit new properties beneficial for man and/or animals.

The above problem has been solved by providing novel microorganisms, namely lactic acid bacteria, belonging to the genus *Lactobacillus* having the traits of being capable of preventing colonization of the intestine with pathogenic bacteria causing diarrhoea and of preventing infection of intestinal epithelial cells by *rotaviruses*. According to a preferred embodiment the *Lactobacillus* strains are capable of adhering to the intestinal mucosa of a host organism and are capable of essentially colonizing it.

According to yet another preferred embodiment the *Lactobacillus* strains are capable to grow in the presence of up to 0.4% bile salts, so that they may easily pass the gastrointestinal tract and stay essentially active.

According to another preferred embodiment the lactic acid bacterium is selected from the group consisting of *Lactobacillus rhamnosus* or *Lactobacillus paracasei*, preferably *Lactobacillus paracasei*, and is more preferably *Lactobacillus paracasei* CNCM I-2116. The microorganisms of the present invention have been shown to exhibit the following properties, they are gram positive, catalase negative, NH3 form arginine negative and CO2 production negative. They produce L(+) lactic acid, are capable to grow in the presence of bile salts in a concentration of up to about 0.4% and may essentially prevent infection of epithelial cells by *rotaviruses*.

The novel microorganisms may be used for the preparation of a variety of ingestable support materials, such as e.g. milk, yogurt, curd, fermented milks, milk based fermented products, fermented cereal based products, milk based powders, infant formulae and may be included in the support in an amount of from about $10^5$ cfu/g to about $10^{11}$ cfu/g. For the purpose of the present invention the abbreviation cfu shall designate a "colony forming unit" that is defined as number of bacterial cells as revealed by microbiological counts on agar plates.

The present invention also provides a food or a pharmaceutical composition containing at least one of the *Lactobacillus* strains having the above traits.

For preparing a food composition according to the present invention at least one of the *Lactobacillus* strains according to the present invention is incorporated in a suitable support, in an amount of from about $10^5$ cfu/g to about $10^{11}$ cfu/g, preferably from about $10^6$ cfu/g to about $10^{10}$ cfu/g, more preferably from about $10^7$ cfu/g to about $10^9$ cfu/g.

In case of a pharmaceutical preparation the product may be prepared in forms of tablets. liquid bacterial suspensions, dried oral supplements, wet oral supplements, dry tube feeding or a wet tube feeding etc., with the amount of *Lactobacillus* strains to be incorporated therein being in the range of up to $10^{12}$ cfu/g, preferably from about $10^7$ cfu/g to about $10^{11}$ cfu/g, more preferably from about $10^7$ cfu/g to about $10^{10}$ cfu/g.

The activity of the novel microorganisms in the individual's intestine is naturally dose dependent. That is, the more the novel microorganisms are incorporated by means of ingesting the above food material or the pharmaceutical composition the higher the protective and/or curing activity of the microorganisms. Since the novel microorganisms are not detrimental to mankind and animals and have eventually been isolated from baby feces a high amount thereof may be incorporated so that essentially a high proportion of the individual's intestine will be colonized by the novel microorganisms.

DETAILED DESCRIPTION OF THE INVENTION

During the extensive studies leading to the present invention the inventors have investigated baby feces and isolated a variety of different bacterial strains therefrom. These strains were subsequently examined for their capability to prevent infection of epithelial cells with *rotaviruses* and pathogenic bacteria known to cause diarrhoea.

Several bacterial genera comprising *Lactobacillus, Lactococcus, Streptococcus* were screened for their inhibitory properties. The tests were essentially performed with three *rotavirus* serotypes representing the major etiological agents of human viral diarrhoea (serotypes G1, G3 and G4) and with pathogenic *E. coli* and *salmonella typhimurium* as representatives for pathogenic microorganisms causing diarrhoea in an affected individual.

The various lactic acid bacteria were grown in a suitable medium, such as MRS, Hugo-Jago or M17 medium at temperatures of from about 30 to 40° C. corresponding to their optimal growth temperature. After reaching stationary growth the bacteria were collected by centrifugation and resuspended in physiological NaCl solution. Between the different tests the bacterial cells were stored frozen (−20° C.).

Rotavirus Tests:

The various *rotavirus* stocks were prepared by infection of confluent cell monolayers. The *rotaviruses* were incubated before infection. The cells were infected with 20 tissue culture infectious doses. For assessing anti-rotaviral properties two different protocols were applied. According to one protocol the various bacterial strains were examined for their direct interaction with the *rotavirus* while in the second protocol the bacteria were screened for those strains that interact with cellular *rotavirus* receptors. The first protocol involved contacting the respective bacterial suspension each with a different *rotavirus* strain and incubating in suitable media. Subsequently, the virus-bacterium mixture was applied to a monolayer of cells of the human undifferentiated colon adenoma cells HT-29 and incubation was continued. Virus replication was then assayed. The second protocol involved incubating the respective bacterial suspension first together with a monolayer of cells of the human undifferentiated colon adenoma cells HT-29 and adding the virus subsequently. After continued incubation virus replication was assayed. *Rotavirus* replication may easily be assessed by histo-immunological staining of *rotavirus* proteins in infected cells. A *rotavirus* inhibitory effect was attributed to a given bacterium when the number of infected cells was reduced by 90% in the cell culture inoculated with *rotavirus* plus the indicated bacteria in comparison with cells inoculated only with *rotavirus*.

Out of a total of 260 different bacterial strains primarily isolated merely 9 could be shown to essentially inhibit rotaviral replication. The different bacteria were ascertained to belong to the genus *Lactobacillus* subspecies *rhamnosus* or *paracasei*. One strain, termed *Lactobacillus casei* ST11, that has been deposited in accordance with the Budapest Treaty and has received the deposit numbers NCC 2461 (I-2116), has been shown to be extremely effective in preventing infection of human cells by *rotavirus*. Moreover, this particular strain shows excellent growing properties as may be shown by acidification in different media. The strain also shows good performance as regards the survival rate during storage at low temperatures of about 10° C., which makes it an excellent candidate for being included in food stuff or pharmaceutical compositions to be stored at refrigerator conditions.

Anti-Pathogenic Bacteria Tests:

For assessing anti-bacterial properties the following approaches were chosen. According to one protocol cultured *Lactobacillus* strains of the present invention were examined for their capability to prevent adhesion of pathogenic bacteria causing diarrhoea to intestinal cells or invasion thereof into intestinal cells, respectively. To this end, intestinal cells were contacted with the pathogenic bacteria and the cultured *Lactobacillus* strains of the present invention, and the rate of adhesion, or invasion, respectively, was assessed. According to a second protocol the supernatant of a cell culture of the *Lactobacillus* strains of the present invention was added together with the pathogenic microorganisms to the intestinal cells and the rate of adhesion, or invasion, respectively, was assessed. During the experimentation it could be shown that the cultured *Lactobacilli* and the supernatant proofed to be extremely effective to prevent both adhesion to and invasion into the intestinal cells indicating that metabolic compounds secreted by the novel microorganisms are likely to be responsible for the anti-diarrhoea activity as regards pathogenic bacteria.

In addition to the above finding it could be shown that the strains surprisingly also exhibit anti-allergenic properties in that said strains have an impact on the synthesis of different immunological mediators.

It is generally acknowledged that humoral immune responses and allergic reactions are mediated by $CD^{30}$ T cells bearing the type 2 phenotype (Th2). Th2-cells are characterized by the production of high levels of interleukine 4 (IL-4), a cytokine required for the secretion of IgE, which is the major antibody class involved in allergic reactions.

The differentiation of Th2 cells is impaired by IFN-γ, a particular cytokine that arises from the mutually exclusive Th1 subset of CD4+ T cells. Said Th1 cells are in turn strongly induced by interleukin 12 (IL-12). In contrast thereto IL-10, another cytokine, has been shown to have a strong suppressing impact on the proliferation of Th1 cells and is therefore deemed to play a role in immuno-suppressive mechanisms.

In summary both IL-12 and IL-10 have strong modulatory effects on CD4+ T cell development by influencing the development of the Th1 subset. IL-12 is a key regulatory cytokine for the induction of Th1 differentiation and thus inhibits the generation of Th2 responses. A major pathway for inhibition of Th2 cells is therefore seen in the stimulation of IL-12 synthesis by accessory cells.

It is well known that some components of gram negative bacteria, such as LPS, induce high levels of IL-12 in adherent cells, such as macrophages and dendritic cells. Consistently, it has been found that gram negative bacteria can strongly bias CD4+ T cell differentiation towards the Th1 phenotype.

The microorganism ST11, as an example of the *Lactobacillus* strains of the present invention, has been tested for a potential role in the induction of cytokines involved in the regulation of CD4+ T cell differentiation. In particular, the effect of ST11 on the pheno-type of CD4+ T cells undergoing Th2 differentiation has been studied.

In this respect the capacity of ST11 to induce the synthesis of mRNA encoding these two regulatory cytokines in mouse adherent cells derived from bone marrow was compared with 4 other strains of *Lactobacilli* and with a control of gram negative bacteria (*E.coli* K12). The mRNA was measured by semi-quantitative RT-PCR after 6 hours of incubation of the cells with serial dilutions of bacteria ranging from $10^9$ to $10^7$ cfu/ml.

Although all strains of *Lactobacillus* could induce transcription of IL-12 mRNA to a certain degree, ST11 could be shown to be the strongest inducer, since as a strong PCR signal could be detected even at the lowest bacterial dose. In fact, the capacity of ST11 to induce IL-12 mRNA transcription was as strong as that of *E. coli*. Induction of IL-10 mRNA was in general weaker than for IL-12 mRNA, as only at higher bacterial doses a signal could be detected. Nevertheless, ST11 was the strongest inducer of IL-10 mRNA, as compared to the other *lactobacilli* and the *E. coli* control.

Thus, ST11 is deemed to be efficient in inducing immunoregulatory cytokines involved in CD4+ T cell differentiation. Its strong capacity to induce IL-12 makes it a candidate to inhibit Th2 responses and its measurable IL-10 induction may prevent inflammatory responses.

In addition to the above finding it was also determined whether ST11 exhibits an inhibitory effect on CD4+ T cells undergoing Th2 differentiation and a positive effect on Th1 functions. A well established cell differentiation culture system was utilized, where precursor CD4+ T cells were polyclonally activated and modulated to undergo either Th1 or Th2 differentiation, depending on the type of co-stimuli provided in the culture medium. Th1/Th2 differentiation was induced during a 7-days primary culture, after which the cells were then restimulated for 2 days in a secondary culture containing medium alone and acquisition of a specific phenotype (Th1 or Th2) was assessed by measuring the types of cytokines produced in the supernatant (IFN-γ vs. IL-4).

It is known that precursor CD4+ T cells from mice of the BALB/c background preferentially differentiate to predominant Th2 phenotype (high IL-4, low IFN-γ in the 2ry culture supernatants) after activation under neutral conditions (medium alone in the 1ry culture). This phenotype could be completely reverted to a Th1 pattern (high IFN-γ, low IL4) upon addition of a blocking monoclonal antibody to IL-4 in the 1ry culture.

To investigate a potential role for ST11 on Th2 inhibition, purified precursor CD4+ T cells from BALB/c mice were activated in the presence of bone marrow adherent cells as accessory cells during the 1ry culture. These cells were co-cultured either in medium alone, or in the presence of 1 mg/ml LPS, or $10^8$ cfu/ml ST11, or $10_8$ cfu/ml of another *Lactobacillus*. After this time, the cells were washed and CD4+ T cells were purified once again and restimulated in the 2ry culture in medium alone. Cytokines produced by the differentiated CD4+ T cells were measured after 2 days. As expected, cells differentiated in the presence of medium alone displayed a dominant Th2 phenotype. Addition of ST11 to the 1ry cultures strongly modulated the outcome of Th2 differentiation, as it resulted in an 8-fold decrease in IL-4 production. This inhibition was of similar magnitude as that observed in cultures derived from cells differentiated in the presence of LPS. In contrast, the other *Lactobacillus* strain had no measurable impact on IL-4 levels. Interestingly, IFN-γ levels were not increased upon addition of ST11 in the 1ry cultures.

In summary, ST11 specifically impaired IL-4 production by CD4+ T cells undergoing Th2 differentiation, but did not significantly increase IFN-γ secretion. The fact that ST11 does not increase IFN-γ production may be due to its capacity to induce IL-10 with the consequence that it may keep a low inflammatory impact despite its anti-Th2 activity.

In consequence, it could be shown that ST11 is a *Lactobacillus* strain that has a good anti-Th2 profile which makes it an excellent candidate for its use as a bacterium with anti-allergic, probiotic activity.

The present invention will now be described by way of example.

Media and Solutions:
MRS (Difco),
Hugo-Jago (Tryptone Difco 30 g/l, Yeast Extract Difco 10 g/l, Lactose Difco 5 g/l.
$KH_2PO_4$ 5 g/l, Beef Extract Difco 2 g/l, agar Difco 2 g/l)
M17 (Difco)
M199 (Seromed)
Ringer solution (Oxoid)
PBS (NaCl 8 g/l, KCl 0.2 g/l, $Na_2HPO_4$ 1.15 g/l, $KH_2PO_4$ 0.2 g/l))
Tryptose phosphate broth (Flow)
Trypsin-EDTA solution (Seromed)

Human *rotavirus* Wa (G1 serotype) and simian *rotavirus* SA-11 (G3 serotype) were obtained from P.A. Offit, Children's Hospital of Philadelphia, U.S.A. The DS-1xRRV reassortant virus was obtained from A. Kapikian, NIH Bethesda, U.S.A. The serotype 4 human *rotavirus* Hochi was obtained from P. Bachmann, University of Munich, Germany. *E. coli* DAEC C 1845 was obtained from Washington University, Seattle and *E. coli* JPN15 was obtained from the Center for Vaccine Development of the University of Maryland, USA). The *salmonella typhimurium* strain SL1344 was obtained from the department of microbiology, Stanford University, CA, USA).

EXAMPLE 1

Isolation of Lactic Acid Bacteria from Baby Feces

Fresh feces were harvested from diapers of 16 healthy babies 15 to 27 days old. 1 g of fresh feces was placed under anaerobic conditions for transportation to the laboratory and microbiological analyses were run within 2 hours from sampling by serial dilutions in Ringer solution and plating on selective media MRS agar plus antibiotics (phosphomycine 80 μg/ml, sulfamethoxazole 93 μg/ml, trimethoprime 5 μg/ml) incubated at 37° C. for 48 hours was used to isolate lactic acid bacteria. Colonies were randomly picked up and purified. Physiological and genetic characterisation was performed on the isolates.

EXAMPLE 2

Testing of Strains in Cell Culture for Anti-Rotaviral Activity

Several bacterial genera comprising *Lactobacillus, Lactococcus, Streptococcus* were selected and tested for members which showed anti-*rotavirus* activity in the cell culture inhibition test. The genus *Lactococcus* was represented by a single species (*Lc. lactis*) consisting of two subspecies (*Lc. lactis* supsp. *lactis* and *cremoris*). A total of 30 strains were tested. The *Streptococcus* genus was represented by a single species (*S. thermophilus*) with 45 strains. The *Leuconostoc* and *Propionibacterium* genus were only represented by a single species (6 strains), while the *Enterococcus* and *Staphylococcus* genus was represented by two species each and a total of 17 strains.

In total, 260 bacterial strains were tested for *rotavirus* inhibitory activity.

$1^{st}$ Protocol:

30 μl of bacterial suspension (containing at average $3 \times 10^6$ bacteria) were mixed with 70 μl M199 medium supplemented with 10% tryptose phosphate broth (Flow) and 5% trypsin-EDTA solution (Seromed) (1: 4 diluted in the case of HT-29 cells) and 100 μl of virus in supplemented M199 medium. The virus-bacterium mixture was incubated for 1 hour at 4° C. and for 1 hour at 37° C. Cells of the human undifferentiated colon adenoma cells HT-29 growing as a confluent monolayer in 96-well microtiter plates were washed three times with phosphate-buffered saline (PBS; pH 7.2). The virus-bacterium mixture was applied to the cells and the microtiter plates were incubated for 18 hrs in a $CO_2$ incubator (Heraeus). Virus replication was assayed as described below.

$2^{nd}$ Protocol:

30 μl of the bacterial suspension (supra) were mixed with 70 μl M199 medium supplemented with 10% tryptose phosphate broth (Flow) and 5% trypsin-EDTA solution (Seromed) (1: 4 diluted in the case of HT-29 cells) and applied directly on the cells in the microtiter plates. After one hour incubation at 37° C. 100 μl of virus in supplemented M199 medium was added to the cells in the microtiter plates. The incubation was continued for 18 hrs in a $CO_2$ incubator (Heraeus). Virus replication was assayed as described below.

The *rotavirus* replication was assessed by histo-immunological staining of *rotavirus* proteins in infected cells as described hereafter.

One day after infection, the cell culture medium was discarded from the microtiter plates and the cells were fixed with absolute ethanol for 10 min. Ethanol was discarded, and the plates were washed three times in PBS buffer. Then, 50 μl of an anti-*rotavirus* serum (mainly directed against VP6 protein), produced in rabbits (obtained from the ISREC University of Lausanne) and diluted 1:2000 in PBS were added to each well and incubated for 1 h at 37° C. with a cover slip to prevent desiccation of the wells. The antiserum was discarded afterwards and the plates were washed three times with PBS. Then 50 μl of anti-rabbit immunoglobulin G (IgG) antiserum produced in goats and coupled to peroxidase (GAR-IgG-PO; Nordic) were added at a dilution of 1 : 500 in PBS to each well and the plates were incubated for 1 hour at 37° C. The serum was discarded and the plates were once again washed three times with PBS. Then, 100 μl of the following substrate mixture was added to each well: 10 ml of 0.05 M Tris-hydrochloride (pH 7.8), 1 ml of $H_2O_2$ (30% Suprapur, diluted 1 :600 in $H_2O$; Merck) and 200 μl of 3-amino-9-ethylcarbazole (0.1 g/10 ml of ethanol stored in 200 μl aliquots at −80° C.; A5754; Sigma). The plates were incubated for at least 30 min at room temperature. The substrate was discarded and the wells were filled with 200 μl of $H_2O$ to stop the reaction. Infected cell foci were counted with an inverted microscope (Diavert; Leitz).

Only very few bacterial strains interacted with *rotaviruses*. Merely 9 out of the 260 bacterial cells primarily selected inhibited *rotavirus* replication in at least one protocol. *Lactobacillus paracasei* NCC 2461 (ST11) showed an extremely high activity against Serotype 1 *Rotavirus*, Serotype 3 *rotavirus* SA-11 and Serotype 4 *rotavirus* Hochi.

EXAMPLE 3

Cultivating Caco-2 Cells

For the (pathogenic) bacterial inhibition assays the cell line Caco-2 was utilized as a model of the intestine. This cell line presents features characteristic for intestinal cells such as e.g. polarisation, expression of intestinal enzymes, production of particular structural polypeptides etc.

The cells were grown on three different supports, namely on plastic dishes (25 $cm^2$, Corning) for growth and propagation, on defatted and sterilized 6 well glass plates (22×22 mm, Corning) for the adhesion tests, and on 24 well glass plates (Corning) for the inhibition tests.

After the second day in culture the medium (DMEM) was changed on a daily basis. Before use the medium was supplemented with 100 U/ml penicilline/streptomycine, 1 μg/ml amphoterine and 20% FCS inactivated at 56° for 30 min. Culturing was performed at 37° C. in an atmosphere comprising 90% air and 10% $CO_2$. The cells were splitted every six days. The cells were detached from the walls of the well by treatment in PBS with 0.25% trypsin and 3 mM EDTA at pH 7.2. For neutralizing the effect of trypsin an equal volume of FCS was added to the cell suspension obtained, the mixture was centrifuged (10 min at 1000 rpm) and the pellet was again put in culture. About $3.5 \times 10^5$ cells were transferred to a new culture bottle and cultivated until a confluent monolayer was obtained.

EXAMPLE 4

Cultivating Bacteria

ST11

The bacterial strain has been stored at −20° C. in MRS medium containing 15% glycerol. The strain has been grown under anaerobic conditions in MRS and transferred twice to new media at intervals of 24 hours before use in the inhibition assays. For the assay a concentration of $2 \times 10^9$ cfu/ml was utilized.

The supernatant was collected by centrifugation for 1 hour at 20.000 rpm and the supernatant obtained was subsequently checked for the presence of bacteria.

*E. coli:*

Two *E. coli* strains were used, *E. coli* DAEC C 1845 (Diffuse Adhesion *E. Coli*) and *E. coli* JPN15 (EPEC; Entero-Pathogenic *E. Coli*).

The first passage after thawing was effected on a CFA—Muller Hinton agar, which is suitable to effect expression of adhesion factors by the bacterium.

Before each experiment the bacterial cells were incubated at 37° C. with a transfer to a new medium being effected twice after 24 hours each. Since JPN15 contains the gene for ampicilline resistance said antibiotic was used for selection during growth.

Salmonella:

The *salmonella typhimurium* strain SL1344 was utilized for the experiments, which was grown before usage in LB medium.

EXAMPLE 5

Inhibition Assay for *E. coli*

After the second passage to new medium the pathogenic bacterial strains were marked with radioisotopes using $C^{14}$-acetat at 10 µCi/ml in LB-medium. Incubation of the strains in this medium was performed for 18 hours at 37° C.

The bacterial suspension was subsequently subjected to centrifugation (1041 g, 15 min) so as to eliminate the supernatant with the remaining $C^{14}$-acetate. The pellet was suspended and washed in PBS and the cells were suspended at a concentration of about $_{11}$ g cells/ml in 1% sterile mannose. The mannose is known to inhibit non specific adhesion.

The different pathogenic bacterial strains (*E. coli*) were contacted with a monolayer of the Caco-2 cells (37° C., 10% $CO_2$, 90% air) for 3 hours. The same experiments were carried out using supernatant (obtained by centrifuging at 20.000 rpm for 40 min).

As a control the pathogenic bacteria were contacted with the Caco-2 monolayer without concurrent addition of ST11 or a culture supernatant, respectively.

After 3 hours incubation the medium was changed and the monolayer was washed three times with PBS. Each washing step included 20×stirring of the PBS solution so as to eliminate essentially all of non specific adhesion. The cells were lysed thereafter by addition of 1 ml sodium carbonate and incubation for 40 min at 37° C. After homogenization an aliquot (250 µl) was diluted in 5 ml scintillation fluid (Hionic-fluor Packcard) and counted (Packard 2000). The percentage of the adhesion of pathogenic cells to Caco-2 cells was calculated against the control, which was set to 100% (adhesion; or invasion for example 6).

EXAMPLE 6

Inhibition Assay for *Salmonella*

*Salmonella* are bacteria that invade epithelial cells and multiply therein. For determining the inhibitory activity of ST11 the *salmonella typhimurium* strain SL1344 was incubated as described above in a medium containing $^{14}C$-acetate and was subjected to the experiment described in example 5.

After incubation the Caco-2 cells were washed with PBS so as to eliminate all non-adhering cells. Subsequently medium was added containing gentamycin (20 µg/ml) and incubation was continued for 1 hour at 37° C. Gentamycin is an antibiotic not penetrating intestinal cells so that all extracellular microorganisms were killed, while *salmonella* having already invaded intestinal cells will survive. After washing the cells twice with PBS the cells were lysed by addition of sterile distilled water and the radioactivity was measured as described in example 4.

The results of experiments 5 and 6 are shown in FIGS. 6 to 9. It may be seen that cultured ST11 cells and the culture supernatant were extremely effective in preventing adhesion of and invasion into intestinal cells by pathogenic microorganisms causing diarrhoea

EXAMPLE 7

Properties of ST11

ST 11 has been subjected to incubation in simulated gastric juice. The simulated gastric juice was prepared by suspending pepsin (3 g/l) in sterile saline (0.5%w/v) and adjusting the pH to 2.0 and pH 3, respectively, with concentrated HCl. ST 11 has been grown in varying amounts in the above media and the resistance of the microorganisms has been determined.

The results are summarized in table I below.

TABLE I

| pH | cfu/ml at T 0 | cfu at T 1 min | Cfu at T 15 | cfu at T 30 | cfu at T 60 |
|---|---|---|---|---|---|
| 2.0 | $2.0 \times 10^9$ | $1.8 \times 10^9$ | $1.2 \times 10^9$ | $3.7 \times 10^8$ | $7.0 \times 10^3$ |
| 3.0 | $2.0 \times 10^9$ | $1.9 \times 10^9$ | $1.7 \times 10^9$ | $1.7 \times 10^9$ | $8.4 \times 10^8$ |

ST11 has the following properties as defined according to methods disclosed in the genera of lactic acid bacteria, Ed. B. J. B. Wood and W. H. Holzapfel, Blackie A&P.

gram positive, catalase negative, $NH_3$ form arginine negative $CO_2$ production negative production of L(+) lactic acid growth in the presence of bile salts in a concentration of up to about 0.4%.

EXAMPLE 8

Growth of St 11 Under Different Conditions

Figure 1:
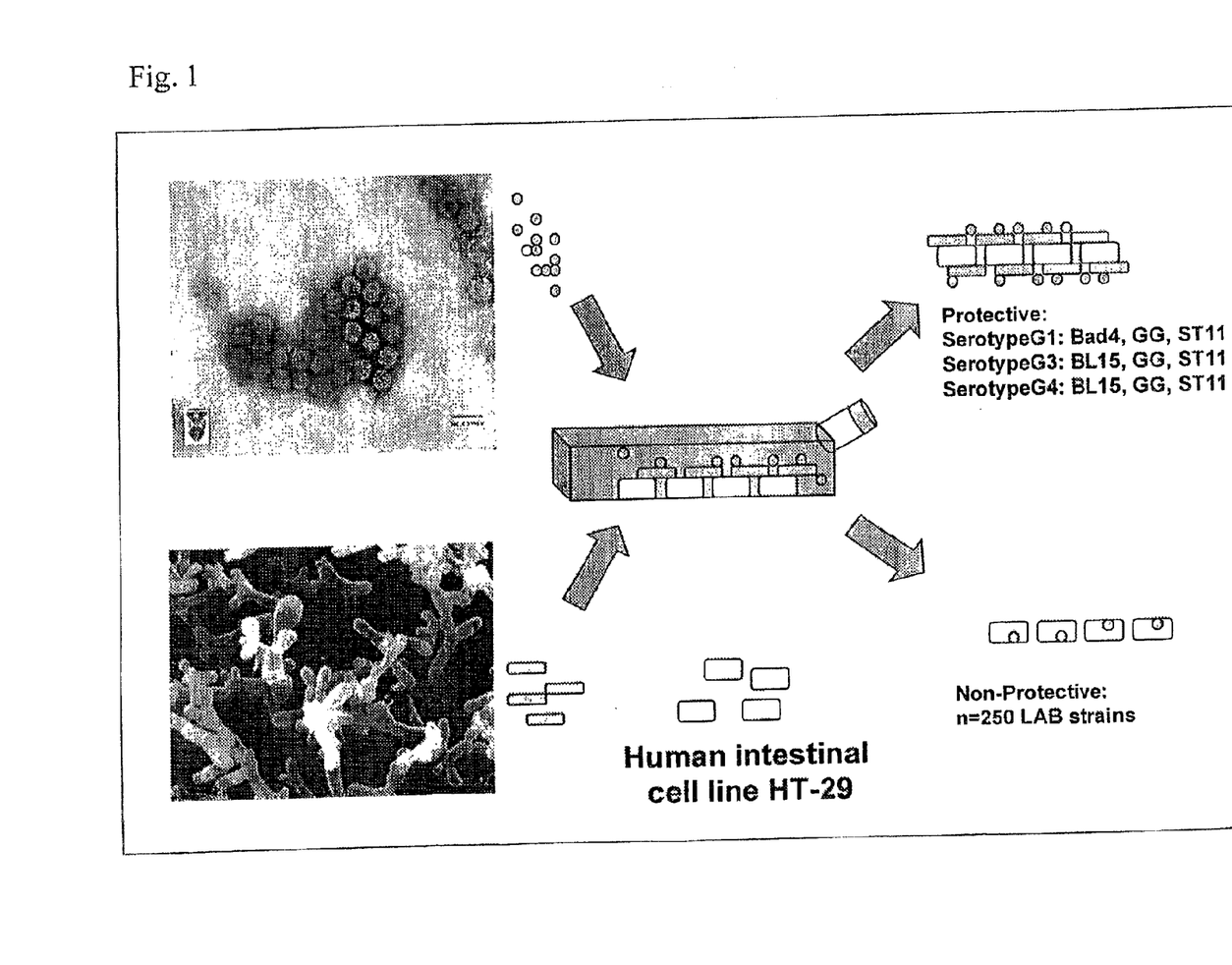
FIG. 1 shows a scheme illustrating the cell culture screening for assessing rotaviral protective properties of bacterial strains.
Figure 2:
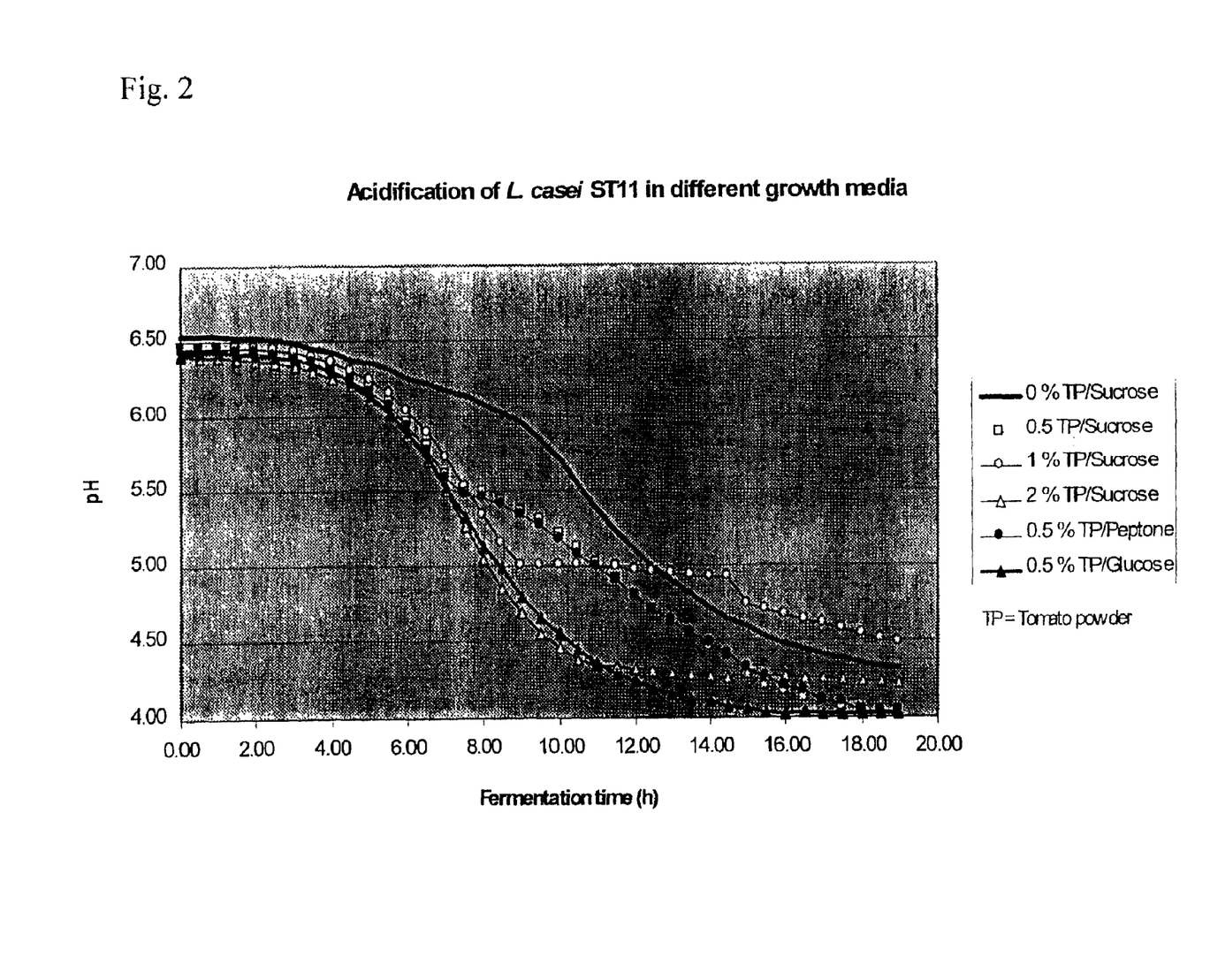
FIG. 2 shows the acidification of the *L. casei* strain CNCM I-2116 (termed ST11) in different growth media.
Figure 3:
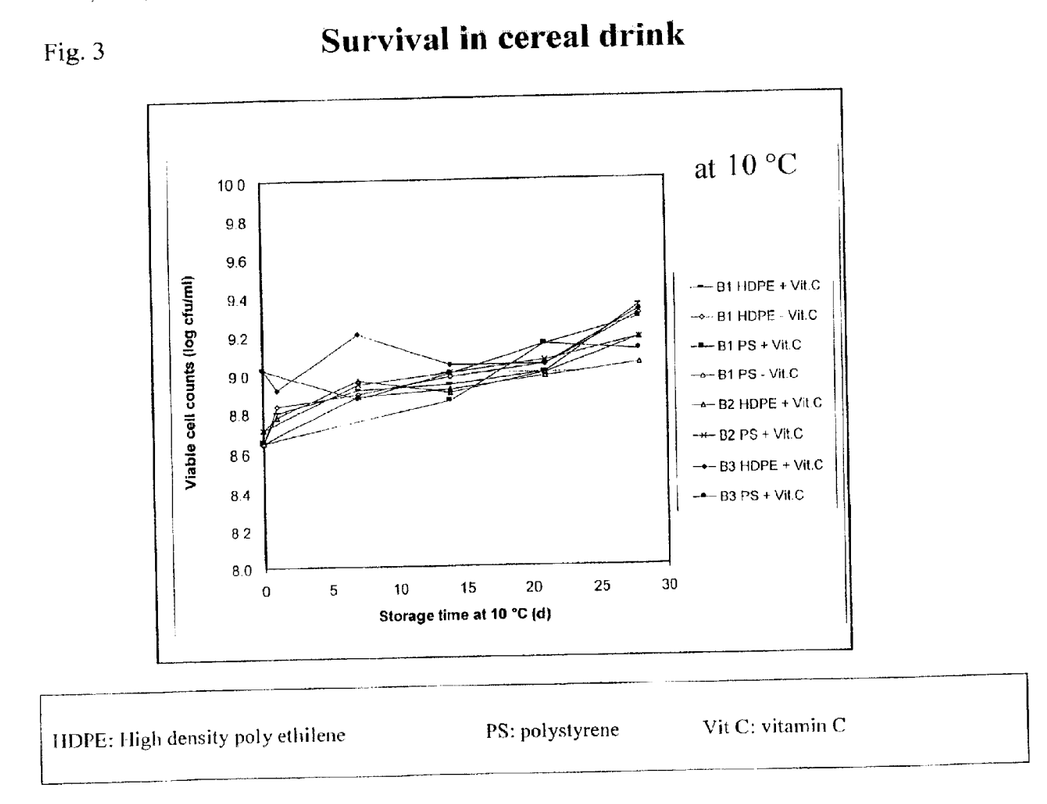
FIG. 3 shows the survival rate of the *L. casei* strain ST11 at 10° C. measured during 30 days.

ST11 was incubated at 37° C. in tomato based medium (4% tomato powder rehydrated in distilled water) supplemented with sucrose (0, 0.5, 1 or 2%) or soya peptone (0.5%) or glucose (0.5%) for different periods of time. The results are shown in FIG. 2.

ST 11 was further added in an amount of 2.5% to a medium composed of rice flour (3%), wheat flour (2%) and sucrose (3%) and incubated at 37° C. until a pH of 4.4 was reached. After cooling the product was packed with or without addition of vit.C and stored at 10° C.

EXAMPLE 9

Induction of IL-12 and IL-10 mRNA Synthesis in Mouse Adherent Cells by St11

Bone marrow cells were isolated from the femur and tibia of 8 week-old specific pathogen-free C57BL/6 mice and were incubated at a concentration of $2 \times 10^6$ cells/ml in RPMI medium (Gibco) containing 10% fetal bovine serum, 1 mM L-Glutamine, 12 mM Hepes, 0.05 mM 2-mercaptoethanol, 100 U/ml penicillin and 100 µg/ml streptomycin (all reagents from Gibco) for 12 hours at 37° C. in a 5% $CO_2$ atmosphere. Non-adherent cells were discarded by 3 consecutive washes with warm culture medium and the remaining adherent cells were harvested and incubated at a concentration of $10^6$ cells/ml for 6 hours in the presence or absence of bacteria. It was previously determined that 6 hours represents an optimal time-point for cytokine mRNA synthesis by mouse adherent cells in response to LPS. Bacteria were added at different concentrations ranging from $10^9$ to $10^7$ cfu/ml. Bacteria were grown and stored as indicated above (page 6).

At the end of the 6-hour culture period, cells were isolated by centrifugation and lysed using the TRIzol reagent kit (GibcoBRL, Cat. No. 15596-018) following the manufacturer's instructions. Total RNA was isolated by isopropanol precipitation and reverse-transcribed into cDNA for 90 min at 42° C. using 200 U reverse transcriptase (Superscript II, BRL) in a 40-µl reaction volume containing 200 mM Tris pH 8.3, 25 mM KCl, 1 µg/ml oligo d(T)$_{15}$ (Boehringer Mannheim), 1 mM DTT (3Boehringer Mannheim), 4 mM of each dNTP (Boehringer Mannheim) and 40 U/ml Rnasin (Promega). PCR primers and conditions were used as already described in Kopf et al. (Journal of Experimental Medicine 1996 Sep. 1; 184(3):1127-36). Amounts of cDNA were normalized within the samples using primers specific for a house-keeping gene (0-2-microglobulin). PCR products were separated on a 2% agarose gel and bands were analyzed under UV.

Figure 4:
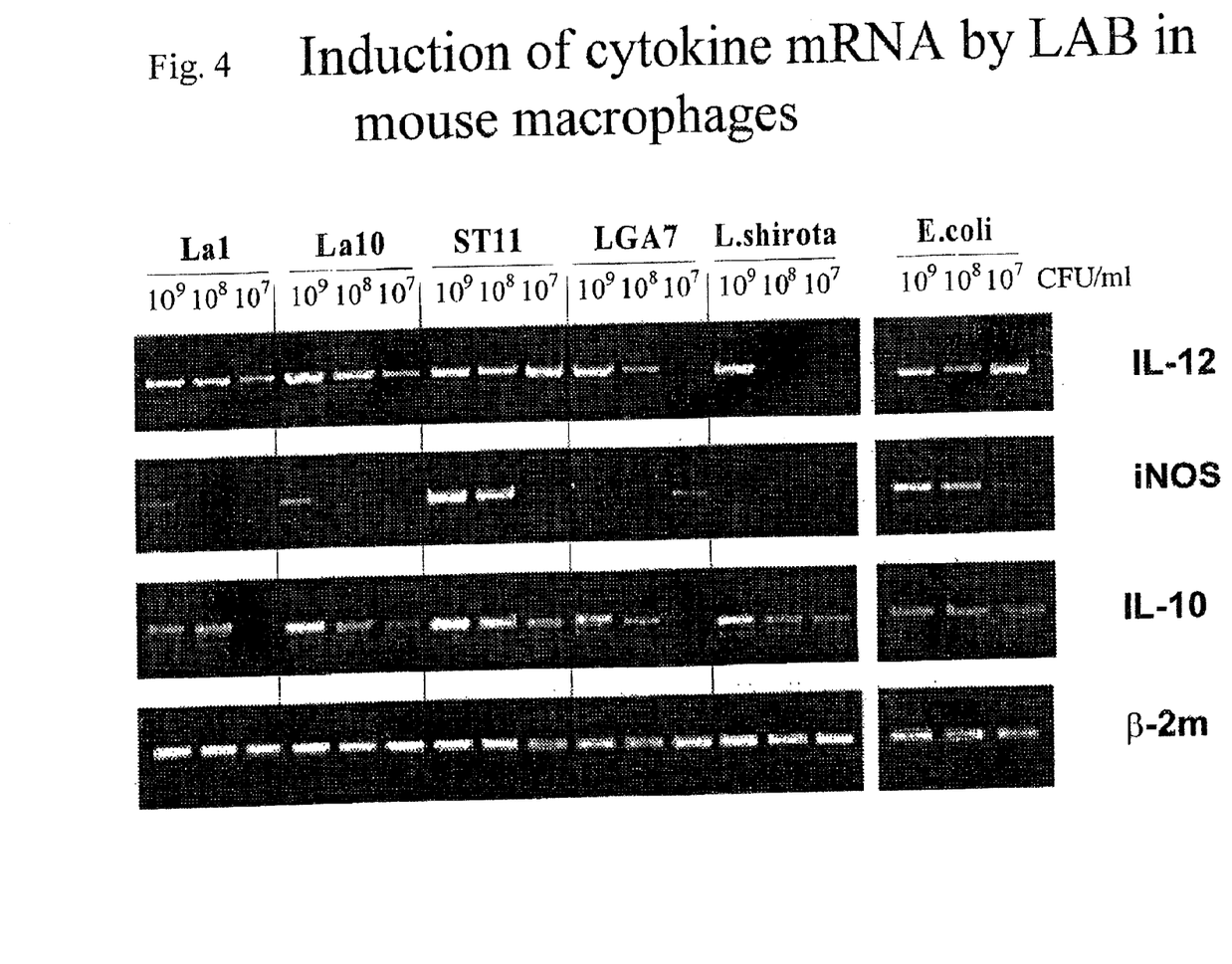
FIG. 4 shows the mRNA pattern of IL-12 and IL-10 in mouse adherent cells derived from bone marrow after incubation of the cells with serial dilutions of ST11.

As shown in FIG. 4, ST11 showed the strongest induction of IL-12 and IL-10 mRNA, which was comparable to levels observed with the positive control (*E. coli*). Differences are best seen at the lowest bacteria concentrations ($10^7$ cfU/Ml).

EXAMPLE 10

Suppression of IL-4 Synthesis by ST11

CD4$^+$ T cells were purified from the spleen of specific pathogen-free BALB/c mice using the MiniMACS kit from Miltenyi Biotec (Cat. No. 492-01). The CD4$^+$ T cells were cultured at a concentration of $2 \times 10^5$ cells/ml in RPMI medium containing 10% fetal bovine serum, 1 mM L-Glutamine, 12 mM Hepes, 0.05 mM 2-mercaptoethanol, 100 U/ml penicillin and 100 µg/ml streptomycin and activated during one week by cross-linking with plate-bound monoclonal antibodies to CD3 (clone 2C11) and CD28 (clone 37.51, both antibodies from Pharmingen). During this Iry culture, the CD4$^+$ T cells were co-cultured with bone marrow adherent cells (isolated as described above) as accessory cells and with $10^8$ cfu/ml ST11, or $10^8$ cfu/ml La1, or 1 mg/ml LPS, or medium alone. After this time, the cells were washed and CD4$^+$ T cells were purified once again using MiniMACS kit technology and restimulated in a 2ry culture containing medium alone. Cytokines produced by the differentiated CD4$^+$ T cells were measured in the supernatants after 2 days using sandwich ELISA (kits from Endogen and Pharmingen).

Figure 5:
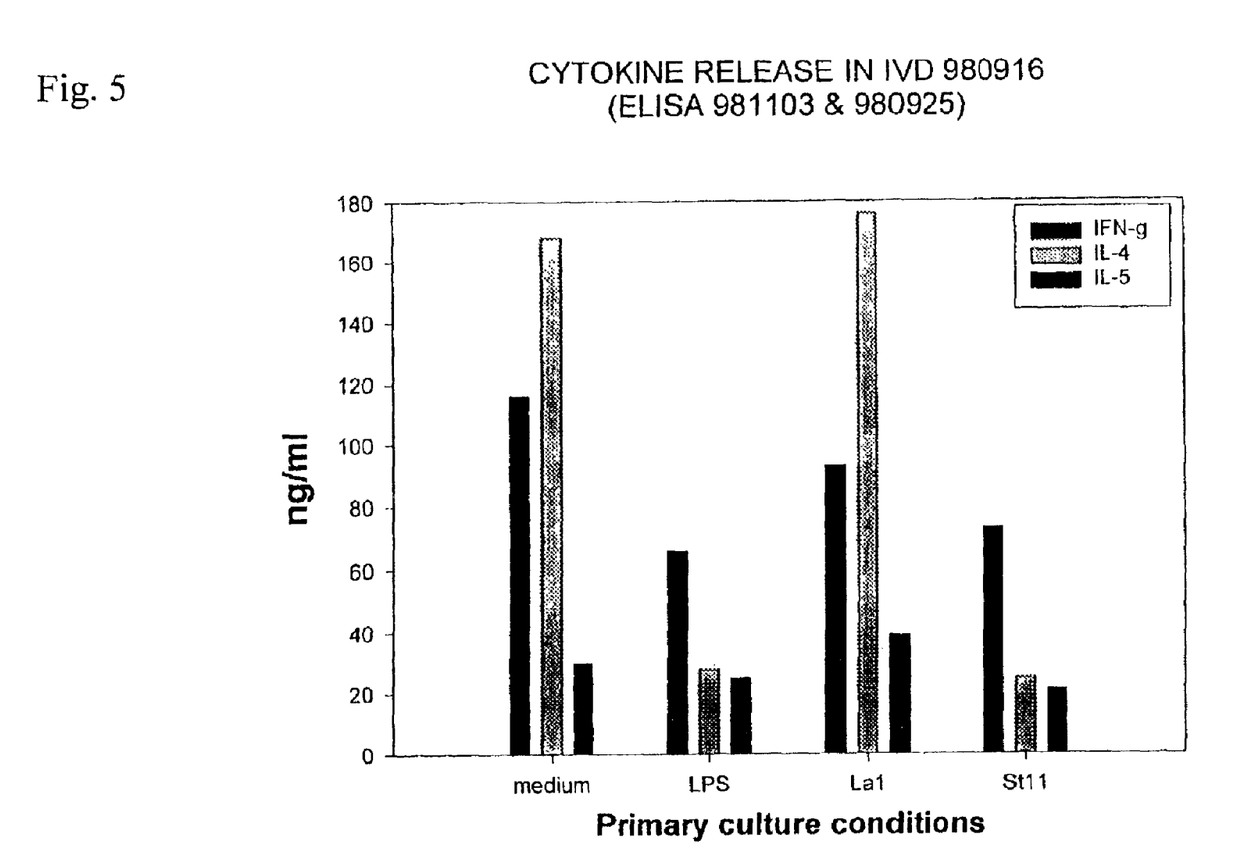
FIG. 5 shows the outcome of Th2 differentiation as resulting in decreased IL-4 production.
Figure 6:
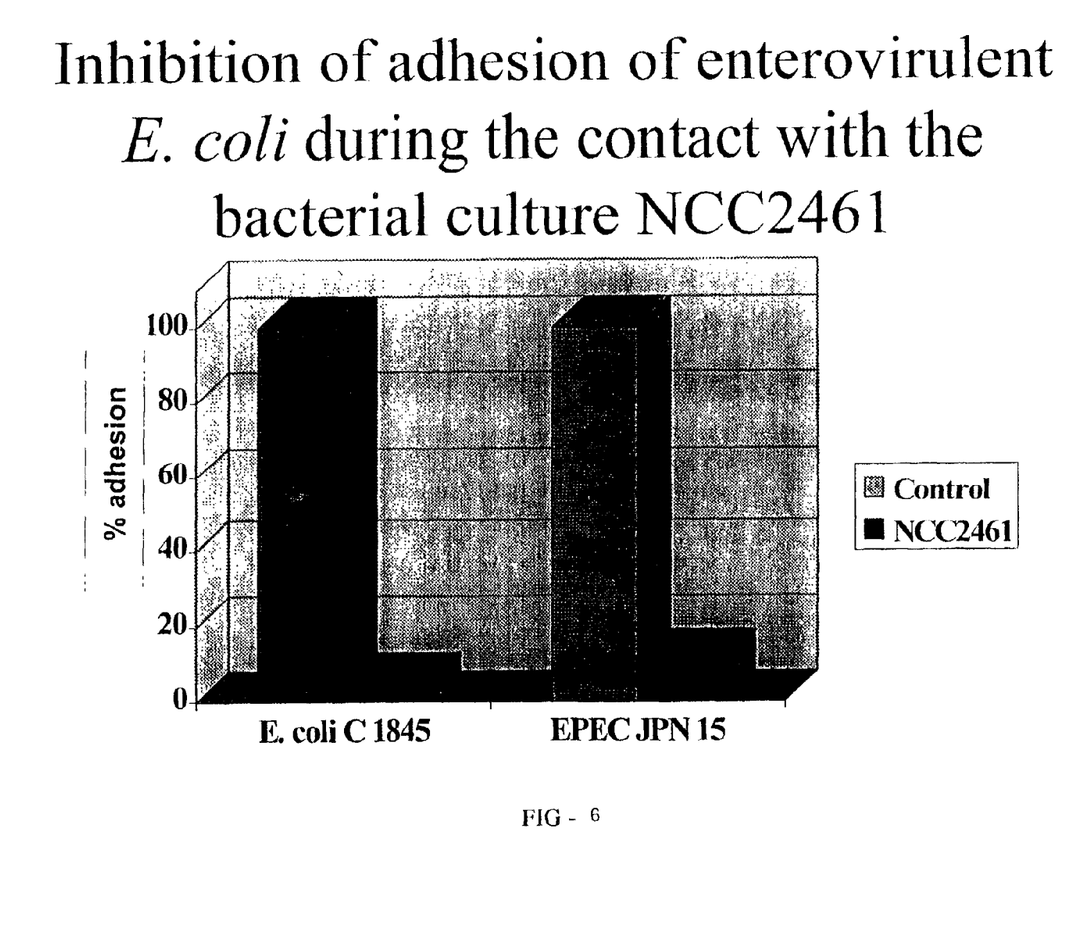
FIG. 6 shows a scheme illustrating the results of a cell culture experiment in which cultured ST11 cells were used in an assay for inhibiting adhesion of pathogenic *E. coli* bacteria to epithelial cells.
Figure 7:
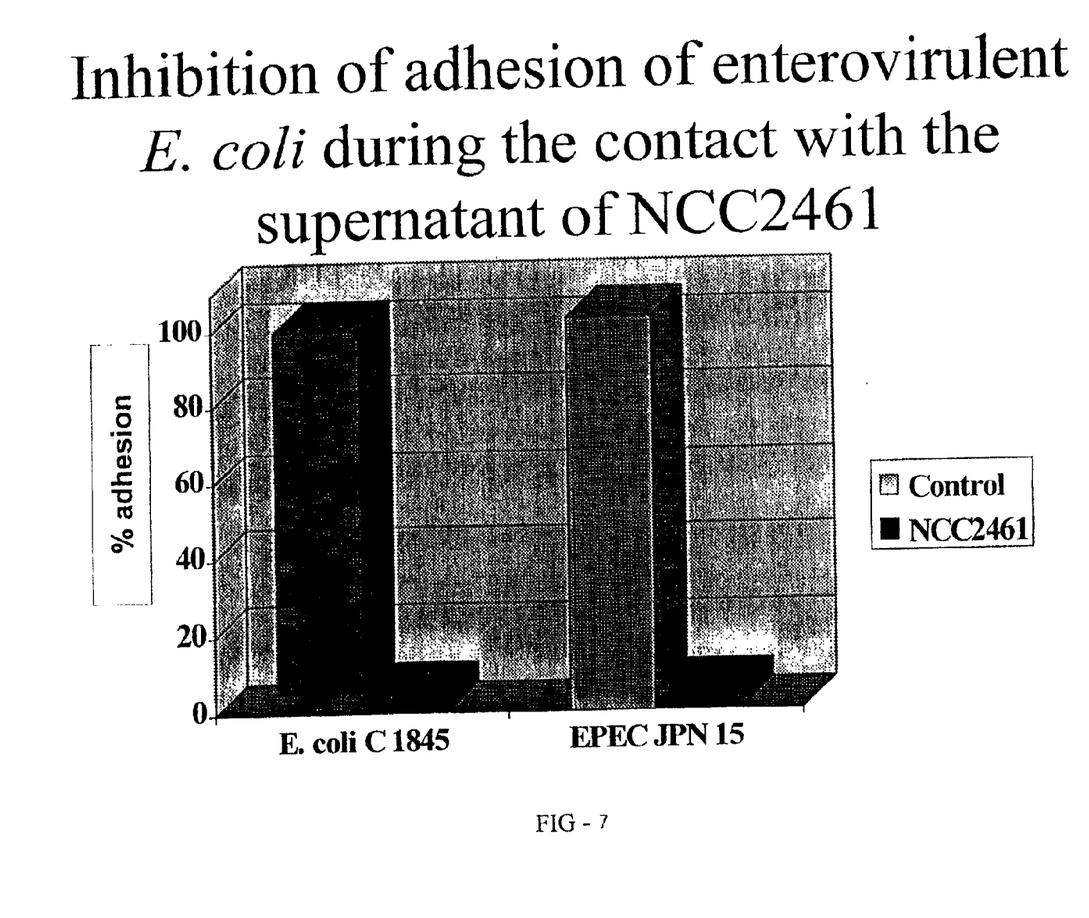
FIG. 7 shows a scheme illustrating the results of a cell culture experiment, in which the supernatant of a ST11 culture was used in an assay for inhibiting adhesion of pathogenic *E. coli* bacteria to epithelial cells.
Figure 8:
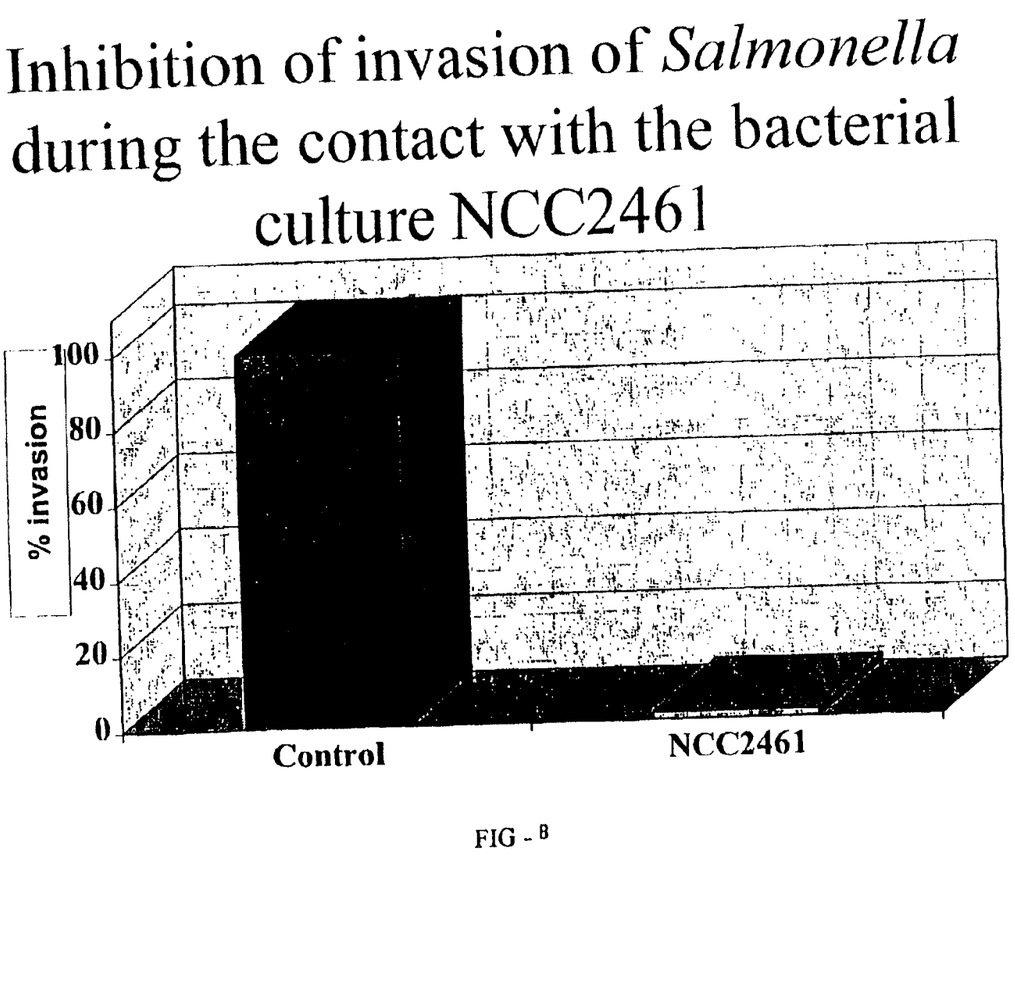
FIG. 8 shows a scheme illustrating the results of a cell culture experiment, in which cultured ST11 cells were used in an assay for inhibiting invasion of *salmonella typhimurium* into epithelial cells.
Figure 9:
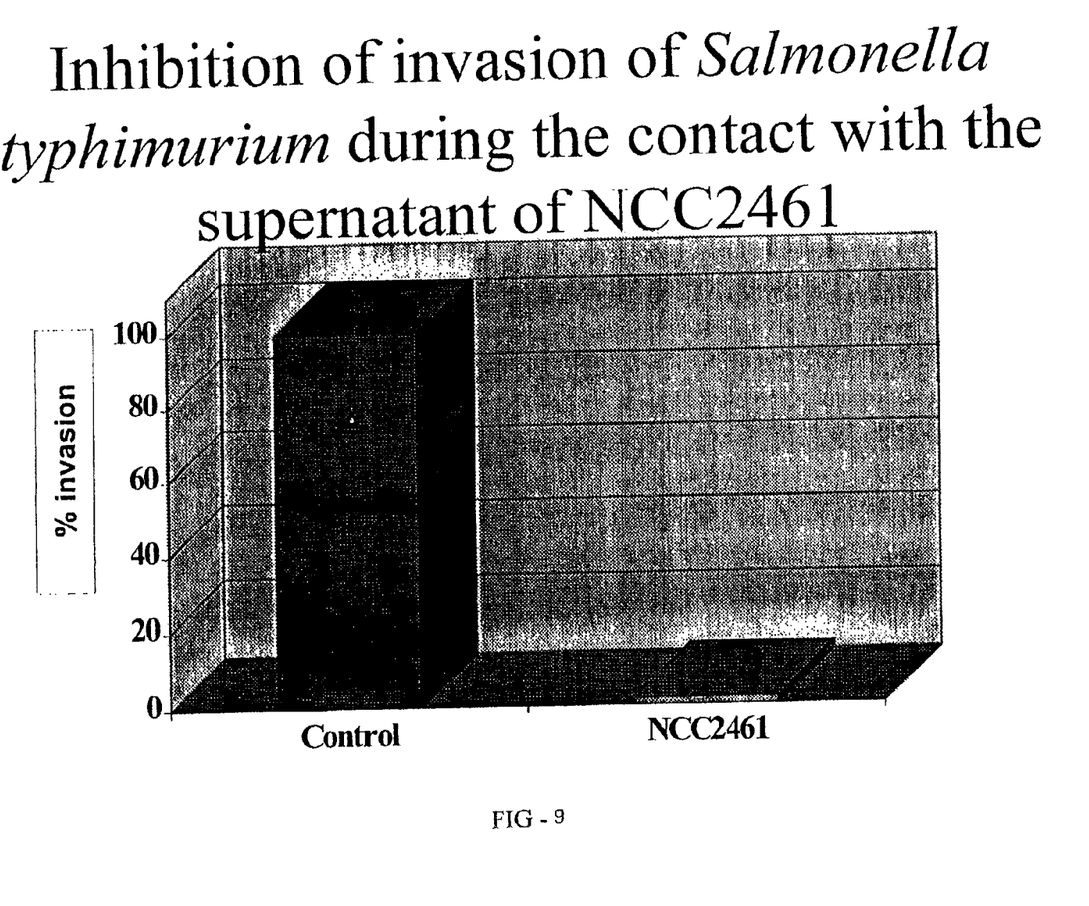
FIG. 9 shows a scheme illustrating the results of a cell culture experiment, in which the supernatant of a ST11 culture was used in an assay for inhibiting invasion of *salmonella typhimurium* into epithelial cells.

Results are shown in FIG. 5. Cells differentiated in the presence of medium alone displayed a dominant Th2 phenotype characterized by high levels of IL4. Addition of ST11 to the 1$^{ry}$ cultures strongly modulated the outcome of Th2 differentiation as it resulted in an 8-fold decrease in IL-4 production. This inhibition was of similar magnitude as that observed in cultures derived from cells differentiated in the presence of LPS. In contrast thereto, the other *Lactobacillus* strain had no measurable impact on IL-4 levels. Interestingly, IFN-γ levels were not increased upon addition of ST11 in the 1$^{ry}$ cultures.

As may be seen from the above the strains of the present invention may be well prepared for the production of a food and/or a pharmaceutical carrier taking advantage of the valuable properties of the microorganisms.

EXAMPLE 11

The ST11 strain was tested in a clinical trial in a community on the outskirts of Guatemala City on its ability to influence the transmission and experience of acute rainy-season diarrhoeal disease experienced by most of the children in this area A total of 203 children, aged 35 to 70 months were enrolled in the study and received a target dose of $10^{10}$ viable organisms (ST11) or none (placebo) over a feeding period of 29 days. The children selected for both sample and placebo, respectively, had the typical deficits in weight-for-age and height-for-age characteristic due to undernutrition.

Before initiating the feeding trial in preschool children, a safety evaluation was conducted based on in vitro and in vivo studies. In vitro studies showed antibiotic resistance pattern similar to those of other *lactobacilli* used in food applications, and no potential for forming biogenic amines, for degrading mucin and for deconjugating bile salts. In a placebo-controlled clinical study involving 42 adult volunteers, ST11 was well tolerated and did not induce any adverse effects, among the potential manifestations monitored, such as flatulence, number of stools per day and stool consistency; the levels of acute-phase proteins in serum did not raise any concern with respect to a potential inflammatory reaction.

The samples and placebo's have been packed in sachets at the Nestle Product Technology Center manufacturing facility in Konolfingen, Switzerland, and shipped refrigerated to Guatemala. Each 10 g sachet consisted of a chocolate flavored vehicle and either 0.2 g of ST11 ($10^{10}$ cfu) or, in case of the placebo, 0.2 g milk powder. The chocolate flavored vehicle consisted of cocoa powder, sugar, soy lecithin, vanillin, and cinnamon. The sachets were stored at 4° to 6° C. until two hours before use. Before use the sachet had to be dissolved in 100 ml water provided by Nestle, which was free of any bacterial contamination.

According to the protocol applied diarrhoea was defined as the occurrence of three or more liquid or unformed fecal evacuation during a period of 24 hrs. A diarrhoeal episode was defined as an event that presented the evidence of diarrhoea (3 diarrhoeal evacuations over 24 hrs). Its total duration in hrs was calculated from the moment of the first of the three index stools to the appearance of the first formed stool or a period 24 h without any defecation. For a child to have a "new" episode, 48 hours had to have elapsed the termination of the prior episode. If not, it was considered a continuation of the same episode and the total duration was then used for evaluation. A case was a child who experienced one or more documented episodes of diarrhoea through the 29-ay observation period. Intensity of a diarrhoeal episode was based on the total number of loose stools produced. The elements of severity of the episode embraced the presence of blood, mucus or pus in stools, along with symptoms of fever and vomiting. An intensity of 7 stools per 24 h or the need for intervention by a health professional at a clinic, health center or hospital also classified an episode as severe.

When a diarrhoeal episode was diagnosed through the surveillance system, a specimen of a diarrhoeal stool was collected for microscopic examination and culture to identify potential etiological pathogens for that episode. The specimen was diagnosed for *rotavirus* antigen, *Giardia*, and *E. histolytica*, in case the sample was dysenteric, and for bacterial pathogens including *Shigella, Salmonella, Aeromonas, Plesiomonas shigelloides, E. Coli* and possibly *V. cholerae*.

During the period of investigation product samples were collected to examine the viability of the microorganisms included during the period of administration. It could be shown that the microorganism stayed viable in the sachets during the entire study so that also at the end of the study the sachets were capable to convey $10^{10}$ viable microorganism upon reconstitution with water.

The study revealed that the sample containing the probiotic microorganism could decrease the occurrence of diarrhoea in contrast to the control group (placebo) by about 30%. Yet, also the control group already exhibited a decreased number of diarrhoeal occurrence over the normal population receiving none of the samples or placebo, respectively. This latter finding may in part be explained on the basis of the children receiving additional valuable nutrition and contamination free water. However, since the study was performed in the field it may clearly be derived that ST11 can surely reduce the occurrence of diarrhoea in vivo.

What is claimed is:

1. A method for preparing an ingestable support material comprising adding to said ingestible support material a biologically pure culture of *Lactobacillus paracasei* CNCM I-2116 having the ability of preventing colonization of an intestine with pathogenic bacteria causing diarrhoea and of preventing infection of intestinal epithelial cells by *rotaviruses*.

2. The method according to claim 1, wherein said strain is contained in said ingestable support material in an amount from about $10^5$ cfu/g to about $10^{12}$ cfu/g of the support material.

3. The method according to claim 1 wherein the ingestable support material is a food composition selected from the group consisting of milk, yogurt, curd, cheese, fermented milks, milk-based fermented products, ice-creams, fermented cereal based products, milk based product, and infant formulae.

4. A method for preparing an ingestable support material comprising adding to said support material a supernatant of a biologically pure culture of *Lactobacillus peracasei* CNCM I-2116 having the ability of preventing colonization of an intestine with pathogenic bacteria causing diarrhoea and of preventing infection of intestinal epithelial cells by *rotaviruses*.

5. The method according to claim 4, wherein the ingestable support material is a food composition selected from milk, yogurt, curd, cheese, fermented milks, milk based fermented products, ice-creams, fermented cereal based products, milk based powders, and infant formulae.

6. A method for treatment of a disorder associated with diarrhoea comprising administering to a patient having the disorder associated with diarrhoea a biologically pure culture of lactic acid bacterium strain *Lactobacillus paracasei* CNCM I-2116 having the ability of preventing colonization of an intestine with pathogenic bacteria causing diarrhoea and of preventing infection of intestinal epithelial cells by *rotaviruses*.

7. The method according to claim 6, wherein the lactic acid bacterium strain is part of a composition which is selected from the group consisting of milk, yogurt, curd, cheese, fermented milks, milk based fermented products, ice-creams, fermented cereal based products, milk based powders, infant formulae, tablets, liquid bacterial suspensions, dried oral supplement, liquid oral supplement, dry tube feeding, and liquid tube feeding.

8. A method for preventing a disorder associated with diarrhoea in a patient at risk of same comprising administering to said patient a biologically pure culture of lactic acid bacterium strain *Lactobacillus paracasei* CNCM I-2116 having the ability of preventing colonization of the intestine with pathogenic bacteria causing diarrhoea and of preventing infection of intestinal epithelial cells by *rotaviruses*.

* * * * *